United States Patent [19]

Rienzo, Sr.

[11] 4,289,136

[45] Sep. 15, 1981

[54] PERCUTANEOUS PAIN ALLEVIATOR METHODS

[76] Inventor: Donald D. Rienzo, Sr., 511 Wolf Hill Rd., Dix Hills, N.Y. 11746

[21] Appl. No.: 94,034

[22] Filed: Nov. 13, 1979

[51] Int. Cl.³ ............................................. A61N 1/36
[52] U.S. Cl. ................................................. 128/421
[58] Field of Search ................... 128/419 R, 421, 422

[56] References Cited

U.S. PATENT DOCUMENTS 3,900,020  8/1975  Lock ................................... 128/422
4,155,366  5/1979  Di Mucci ........................... 128/421

Primary Examiner—William E. Kamm
Attorney, Agent, or Firm—Hane, Roberts, Spiecens & Cohen

[57] ABSTRACT

A method for effecting percutaneous pain alleviation in which right-angled sawtooth shaped electrical pulses are produced at electrodes for percutaneous application to bodily areas experiencing pain. One of the electrodes is located at the site of the pain while the other electrode is moved to different sites of the region of the pain. At the same time the amplitude of the electrical signals is measured for each site until a maximum amplitude site is located. Thereafter, an electrode is continuously positioned at the located site for a given period of time for continuous application of the electrical pulses which may be selectively varied in amplitude in the range of zero to about 100 volts peak-to-peak and the output current controlled from 1 MA to 40 MA, while the pulse repetition frequency may be selectively varied in the range of about 10 HZ to 100 HZ.

5 Claims, 5 Drawing Figures

U.S. Patent      Sep. 15, 1981      4,289,136
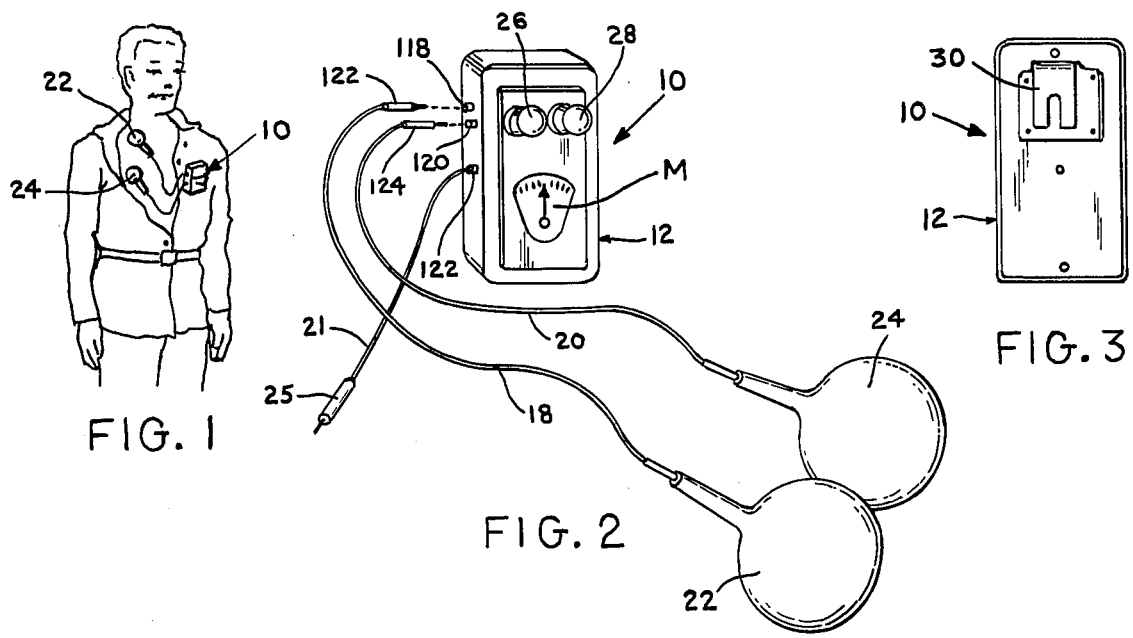
FIG. 1
FIG. 2
FIG. 3
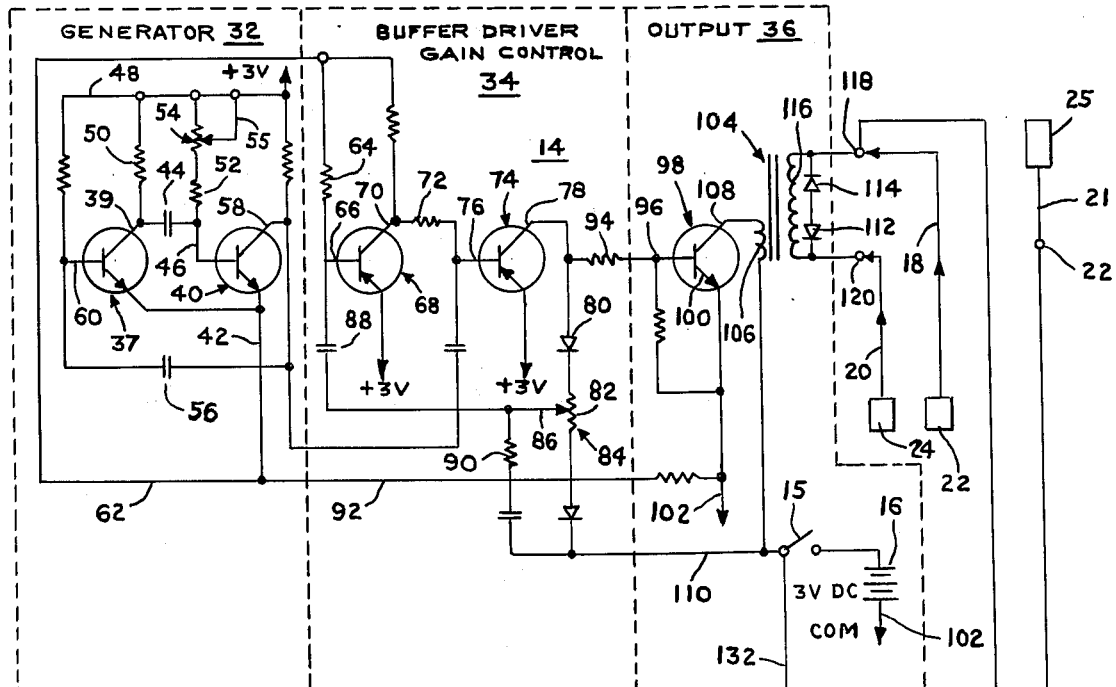
FIG. 4
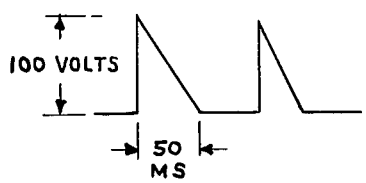
FIG. 5

PERCUTANEOUS PAIN ALLEVIATOR METHODS

BACKGROUND OF THE INVENTION

The present invention relates to methods and apparatus for electrical treatment of body tissues and muscles and more particularly to percutaneous pain alleviation by application of electrical tubes to external areas of the human body experiencing pain.

Electrical pulse generators have long been known for use for various medical purposes. The use of such devices, however, has been limited due to the sometimes painful and noxious side effects produced by such devices. Such undesirable side effects have been variously attributed to excessive voltages, improper pulse frequencies and/or wave shapes and unduly lengthy periods of application of the electrical pulses to the body. The cumbersome and unwieldy bulk and weight of such known devices has further limited the use of such devices at fixed locations, to wit, at the physician's office, the home, etc.

In U.S. Pat. No. 4,155,366 there is disclosed a method or percutaneous pain alleviation in which the amplitude and pulse repetition frequency of the electrical output pulses fed to electrodes for application to the pain site is selectively variable by the user. The method in said patent has created a demand for even better methods and apparatus centering around the positioning of the electrodes.

SUMMARY OF THE INVENTION

Briefly, the invention contemplates a method of alleviating pain at a side of the body by generating periodically recurring electrical pulse signals which are applied to a base electrode and at least one other electrode. The base electrode is positioned at the site of the body experiencing the pain while at least one of the other electrodes is scanningly applied to various portions of the body. At each point of application the amplitude of the electrical pulse signal fed between the base electrode and the one of other electrodes measures so as to determine the point of application yielding the maximum amplitude of electrical pulse signal. Then at least one of the other electrodes is positioned at the indicated point of application for a given period of time, whereby the electrical pulse signals block the pain at that side of the body.

There is also contemplated apparatus for practicing the method.

BRIEF DESCRIPTION OF THE DRAWINGS

Further objects, features and advantages of this invention will become apparent from a consideration of the following description, the appended claims and the accompanying drawing, in which:

FIG. 1 is a pictorial illustration showing the manner of use of the device of the present invention;

FIG. 2 is a front perspective view of the device for carrying out the method of the present invention;

FIG. 3 is a rear view of the device of FIG. 2;

FIG. 4 is an electrical schematic diagram of the device of FIG. 2; and

FIG. 5 is a waveform diagram of the output pulses of the device of FIG. 2.

DETAILED DESCRIPTION OF THE INVENTION

In the drawing and in particular FIGS. 1-3 thereof a percutaneous pain alleviator device for carrying out the present invention is generally designated by the numeral 10.

Device 10 comprises a pocket size housing 12 enclosing an electrical pulse generator 14 including a battery 16 (shown in FIG. 4), a pair of detachable output electrodes 18, 20 respectively terminating in disc-shaped applicator probes 22, 24 of a conductive elastomer, and a further detectable electrode 21 connected to a scanning probe 25. Device 10 is provided with a pair of rotatable control knobs 26, 28 for respectively controlling the magnitude knobs 26, 28 for respectively controlling the magnitude of the output voltage (also output element) and pulse repetition frequency of the output pulses obtained at output electrodes 18 and 20, as well as a meter M.

In addition, housing 12 may be provided with a mounting clip 30 on the back face thereof for convenience in wearing device 10 when attached to a shirt pocket as shown in FIG. 1 or any other suitable article of clothing.

Referring to FIG. 4, pulse generator circuit 14 comprises a generator stage 32, a buffer driver and gain control stage 34, an output stage 36 and an indicator 38.

Generator stage 32 is an emitter-coupled free-running multivibrator comprising a pair of transistors 38 and 40 having their emitters jointly connected by lead 42, with the collector 39 of transistor 38 being connected through coupling capacitor 44 to the base 46 of transistor 40. Collector 39 is connected to bias supply line 48 through resistor 50 while base 46 is connected to supply line 48 through fixed resistor 52 and variable pulse repetition frequency control resistor 54 in series therewith. Coupling capacitor 56 feeds the pulse output at collector 58 of transistor 40 back to the input base 60 of transistor 38.

The pulse output of generator stage 32 appearing on emitter lead 42 is applied through lead 62 and resistor 64 to the input of buffer driver stage 34 at base 66 of transistor 68. The output of buffer transistor 68 taken at collector 70 is applied via resistor 72 to the input of transistor 74 at its base 76. Collector 78 is connected through diode 80 to one end of the resistor arm 82 of gain control potentiometer 84, of which wiper arm 86 is connected to base 66 through coupling capacitor 88 and through resistor 90 to lead 92. The other end of resistor arm 82 is connected to lead 92.

The pulse output from transistor 74 taken at collector 78 is applied via resistor 94 to the base of output transistor 98, while emitter 100 is connected to common terminal 102.

Transformer 104 has its primary winding 106 connected across collector 108 of transistor 98 and bias supply lead 110. The back-to-back arrangement of fiodes 112 and 114 is connected across transformer secondary winding 116, with the output terminal jacks 118 and 120 being taken across secondary winding 116.

Output electrodes 18 and 20 may be releasably connected to output jacks 118 and 120 by means of electrode plugs 112 and 124 affixed to the respective ends of electrodes 18 and 20.

Output jack 118, plug 122 and applicator probe 22 may be colored red signifying the "positive" electrode and jack 120, plug 124 and probe 24 colored black signifying the "negative" electrode.

The pulse output at output terminals 118 (FIG. 5) i a right angle sawtooth waveform with a perpendicular leading edge and a sloped trailing edge and having a selectively variable amplotude ranging from zero to 100 volts peak-to-peak, a selectively variable pulse repetition frequency rangning from 10 HZ to 100 HZ, and a current ranging from 1 to 40 MA. The amplitude may be selectively varied by potentiometer arm 86 which is mechanically connected to voltage amplitude control knob 26, while the pulse repetition frequency (p.r.f.) may be selectively varied by variable resistor 54 whose wiper arm 55 is connected to frequency control knob 55.

The indicator circuit 38 centers around transistor 120 having collector 132 connected to the bias supply lead 110, a base connected to terminal jack 120 and an emitter connected via ammeter M to the system ground COM. A filter capacitor 138 is positioned accross the ammeter M as well as emitter resistor 140. A biasing diode 142 is connected across the emitter 136 and base 134. The base 134 is connected to output jack 120. The common COM is connected to output jack 122 into which is connected electrode 21 having the scanning probe 25 at the end thereof. The circuit operates as a emitter-follower with the voltage at the meter M being equal to the voltage across resistor 140 but as an amplified current value. The capacitor 138 smoothes the pulse signals to a DC voltage level.

A power on-off switch 15 is connected between the positive terminal of battery 16 and lead 110 for selective connection of battery 16 when device 10 is in use and disconnection when not in use.

In operation, it is first necessary to locate the proper points of application of the electrodes. With the electrodes 18 and 21 connected and the electrode 20 removed the wearer applies positive electrode pad 22 directly on the bodily site experiencing pain and the scanning probe 23 (a suitable water soluble jelly can be used) is then moved over the adjacent skin area. (At this time the amplitude and frequency controls are set below mid range.) During this scanning the scale of the ammeter M is observed. When a maximum amplitude is shown, the position of the scanning probe is noted and marked. It has been found that this site is usually on a line which includes the scanning probe 25 the pain site and the head of the user. More often the probe 25 is positioned between the pad 22 on the pain site and the head of the user.

Thereafter, the electrode 21 with probe 25 is removed from jack 122 and electrode 20 with pad 24 is applied to the located site.

The wearer may then adjust the magnitude and frequency of the pulse output being applied by manipulating knobs 26 and 28 respectively until he arrives at an optimum voltage magnitude and p.r.f., which provides the greatest degree of pain relief and freedom from noxious side effects, i.e., greatest comfort. It has been found that pain relief is usually obtained within about fifteen minutes of application of device 10 and that for best results in many instances the application should continue for about fifteen minutes after substantial pain relief is experienced.

Tests have shown that the p.r.f. to be effective without side effects or burns must be in the range of 10 to 100 HZ. In fact, when frequencies in the range of 500 to 5000 HZ have been used skin irritation has been found. In addition, the 10 to 100 HZ range permits the use of multiple sets of electrodes in parallel with the original set of electrodes.

Although the invention has been described with reference to a particular embodiment thereof, it is to be understood that this embodiment is merely illustrative of the application of the principles of the invention. Numerous modifications may be made therein and other arrangements may be devised without departing from the spirit and scope of the invention.

I claim:

1. The method of alleviating pain at a portion of the body of a user comprising the steps of generating periodically recurring electrical pulse signals, applying said pulse signals to a base electrode and at least one other electrode, positioning the base electrode at the site of the body experiencing the pain, scanningly applying one of said other electrodes to various portions of the body, at each point of application measuring the amplitude of the electrical pulse signals fed between said base electrode and said one of said other electrodes, indicating the point of application yielding the maximum amplitude of the electrical pulse signals, thereafter positioning at least one of said other electrodes at the indicated point of application for a given period of time while said base electrode remains positioned at the site of the body experiencing the pain, whereby the electrical pulse signals block the pain at that site of the body.

2. The method of claim 1, after said electrodes are positioned at the site of the body experiencing pain and at the indicated point of application, varying the amplitude of the electrical pulse signals to achieve the desired blocking.

3. The method of claims 1 or 2 wherein the electric pulse signals has a right-angled sawtooth waveform.

4. The method of claim 1 wherein the scanningly applying step applies said one electrode such that the pain site, said one electrode and the head of the user are in a line.

5. The method of claims 1 or 4 wherein the scanning applying step applies said one electrode at a point between the pain site and the head of the user.

* * * * *